United States Patent
Hong

(10) Patent No.: US 11,180,469 B2
(45) Date of Patent: Nov. 23, 2021

(54) METHOD FOR PREPARING SULTONE DERIVATIVES

(71) Applicant: Samhwa Paints Industries Co., Ltd., Seonggok-dong (KR)

(72) Inventor: Myeng Chan Hong, Pyeongtaek-si (KR)

(73) Assignee: Samhwa Paints Industries Co., Ltd.

( * ) Notice: Subject to any disclaimer, the term of this patent is extended or adjusted under 35 U.S.C. 154(b) by 400 days.

(21) Appl. No.: 16/450,178

(22) Filed: Jun. 24, 2019

(65) Prior Publication Data

US 2020/0002308 A1   Jan. 2, 2020

(30) Foreign Application Priority Data

Jun. 27, 2018 (KR) .................. 10-2018-0073716

(51) Int. Cl.
*C07D 327/04* (2006.01)
*H01M 10/0525* (2010.01)
*H01M 10/0567* (2010.01)

(52) U.S. Cl.
CPC ...... *C07D 327/04* (2013.01); *H01M 10/0525* (2013.01); *H01M 10/0567* (2013.01)

(58) Field of Classification Search
CPC .................................................. C07D 327/04
See application file for complete search history.

(56) References Cited

U.S. PATENT DOCUMENTS

| 10,734,680 B2 * | 8/2020 | Yoshida | ............ H01M 10/0569 |
| 2011/0160465 A1 * | 6/2011 | Nakayama | ........... C07D 497/18 549/33 |

FOREIGN PATENT DOCUMENTS

| CN | 106632232 A | * | 5/2017 |
| JP | 05043572 A | * | 2/1993 |
| KR | 101777474 B1 | * | 9/2017 |

OTHER PUBLICATIONS

Machine translation of CN 106632232 (no date).*
Machine translation of JP 05-043572 (no date).*
Mondal, "Recent Developments in the Synthesis and Application of Sultones", Chemical Reviews, 112, 5339-5355 (2012).*

* cited by examiner

*Primary Examiner* — Amanda C. Walke
(74) *Attorney, Agent, or Firm* — McDonnell Boehnen Hulbert & Berghoff LLP

(57) ABSTRACT

The present invention relates to a method for preparing 1,3-propanesultone derivative compounds used for pharmaceutical intermediates, organic solvents, and electrolyte additives for lithium ion secondary batteries. According to the preparation method of the present invention, it is possible to prepare a sultone compound having various derivatives in high yield.

8 Claims, No Drawings

METHOD FOR PREPARING SULTONE DERIVATIVES

TECHNICAL FIELD

The present invention relates to a method for preparing 1,3-propanesultone derivative compounds used for pharmaceutical intermediates, organic solvents, and electrolyte additives for lithium ion secondary batteries.

BACKGROUND ART

Use of electrolyte additives is one of the most economical and effective methods for the improvement of lithium ion battery performance. Solid electrolyte interface (SEI), which is formed on the negative electrode due to decomposition of electrolyte, is the key factor which affects battery performance such as charge/discharge capacity, storage life, cycle life, storage, etc. At this time, the additive serves to aid in or maintain the formation of SEI. Recent market requirements require lithium-ion batteries with higher energy density, higher power, and higher safety. However, for the additives used in the past, there is a problem in that a stable passivation film of a lithium ion battery cannot be achieved and thus a cycle performance cannot be maintained for a long period of time. Therefore, it is necessary to develop a new electrolyte additive for effectively producing a stable electrode passivation film for high-energy and high-voltage lithium ion batteries. Among these additives, sultone compounds are expected to be a stable negative electrode film-forming agent because they are excellent in flame retardance, low temperature characteristics, voltage resistance, high in dielectric constant and thus dissolved in electrolyte salts and excellent in compatibility with hydrocarbon solvents.

On the other hand, in the conventional technique, the use of sultone derivative compounds as organic solvents and electrolyte additives for lithium ion secondary batteries has been reported, but there was no mention of a specific preparation method of the sultone derivative compounds.

In another conventional technique, sultone and sulfuryl chloride were reacted to introduce a chlorine group at position 3 and substituting a fluorine group, thereby synthesizing 3-fluoro-1,3-propane sultone. However, the position for introducing a chlorine group into sultone is limited to the position 2 to 3. Further, when a compound in which a chlorine group is introduced at position 2 is used in the step of substituting a fluorine group, a chlorine removal reaction easily occurs, and thus propene sultone is synthesized.

In still another conventional technique, a method of introducing fluorine atoms at position 3 by reacting sultone with diethylaminosulfur triflouide (DAST) or bis(2-methoxyethyl)aminosulfur triflouroide (BAST) has been introduced. Moreover, although experiments were conducted based on the above-mentioned methods, the reaction did not proceed at all.

Thus, in the conventional techniques, no specific preparation methods are described, and the position for introducing chlorine or fluorine atoms into sultone is limited, which results in limitation to the preparation of various sultone derivatives.

DETAILED DESCRIPTION OF THE INVENTION

Technical Problem

An object of the present invention is to provide a method for preparing a sultone compound having various derivatives in high yield.

Technical Solution

In view of the above, the present inventors have synthesized sultone derivatives by a method of using compounds having both an alcohol functional group as starting materials instead of a conventional substitution reaction using sultone as a starting material, reacting an alcohol with a sulfonyl chloride derivative, and then carrying out a cyclization reaction using a base, thereby completing the present invention.

According to one aspect of the present invention, there is provided a method for preparing a sultone derivative represented by the following Chemical Formula 4, the method comprising the steps of:

1) reacting an alcohol represented by the following Chemical Formula 1 with a sulfonyl chloride derivative represented by the following Chemical Formula 2 to prepare an intermediate represented by the following Chemical Formula 3; and 2) cyclizing the intermediate represented by the Chemical Formula 3 to prepare the sultone derivative represented by the Chemical Formula 4.

[Chemical Formula 1]
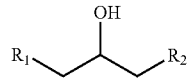

[Chemical Formula 2]
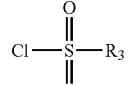

[Chemical Formula 3]
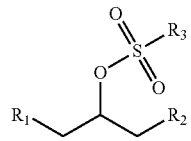

[Chemical Formula 4]
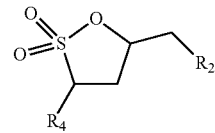

wherein, $R_1$, $R_2$, $R_3$ and $R_4$ represent each independently hydrogen, a halogen atom, an unsubstituted C1-C10 alkyl group or a C1-C10 alkyl group substituted with halogen.

In this case, the first step and the second step may be carried out in the presence of a base.

The base used in the first step may be at least one selected from the group consisting of triethylamine, pyridine, 1-methylimidazole, pyrrolidine, imidazole and morpholine.

In addition, the base used in the second step may be at least one selected from the group consisting of methyl lithium, butyl lithium, sec-butyllithium, tert-butyllithium, lithium diisopropylamide, lithium bistrimethylsilane, lithium tetramethylpiperidine, potassium bistrimethylsilylamide and sodium hydride.

Further, the above reaction can be carried out in the presence of a solvent.

Specifically, the first step and the second step may be carried out in the presence of at least one solvent selected from the group consisting of dichloromethane, tetrahydrofuran, toluene, ethyl acetate and n-hexane.

The first step may be carried out at a temperature of −10 to 30° C., and the second step may be carried out at a temperature of −90 to 10° C.

Further, in Chemical Formulas 1 to 4, $R_1$ and $R_2$ are each independently a halogen atom, and $R_3$ and $R_4$ may be each independently hydrogen, an unsubstituted C1-C4 alkyl group, or a C1-C4 alkyl group substituted with halogen.

Advantageous Effects

According to the preparation method of the present invention, 1,3-propanesultone compounds having various derivatives can be prepared in high yield. In addition, the sultone derivatives prepared according to the preparation method of the present invention can be effectively applied to various applications such as electrolyte solution of lithium ion secondary battery, medicines, agricultural chemicals, fine chemicals, and the like.

DETAILED DESCRIPTION OF THE EMBODIMENTS

Hereinafter, embodiments of the present invention will be described in detail.

Specifically, in one embodiment of the invention, there is provided a method for preparing a sultone derivative represented by the following Chemical Formula 4, the method comprising the steps of:

1) reacting an alcohol represented by the following Chemical Formula 1 with a sulfonyl chloride derivative represented by the following Chemical Formula 2 to prepare an intermediate represented by the following Chemical Formula 3; and 2) cyclizing the intermediate represented by the Chemical Formula 3 to prepare the sultone derivative represented by the Chemical Formula 4.

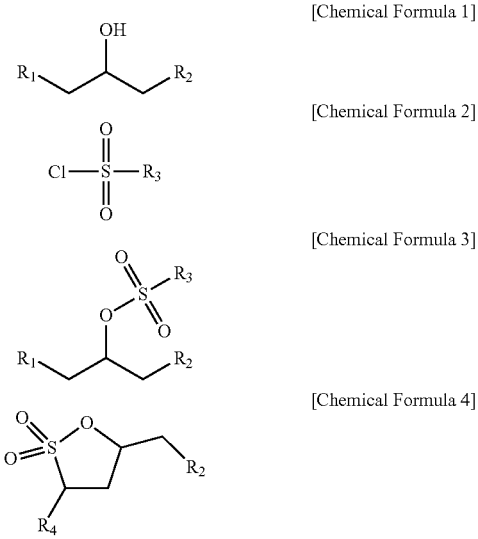

[Chemical Formula 1]

[Chemical Formula 2]

[Chemical Formula 3]

[Chemical Formula 4]

wherein, $R_1$, $R_2$, $R_3$ and $R_4$ represent each independently hydrogen, a halogen atom, an unsubstituted C1-C10 alkyl group or a C1-C10 alkyl group substituted with halogen.

In an embodiment of the present invention, the $R_1$, $R_2$, $R_3$ and $R_4$ are each independently a halogen atom, an unsubstituted C1-C4 alkyl group, a C1-C4 alkyl group substituted with chlorine or fluorine.

In another embodiment of the present invention, the $R_1$ and $R_2$ may be each independently a halogen atom, and the $R_3$ and $R_4$ may be each independently hydrogen, an unsubstituted C1-C4 alkyl group or a C1-C4 alkyl group substituted with halogen.

In another embodiment of the present invention, the $R_1$ and $R_2$ may be each independently F, Cl, Br or I, and the $R_3$ and $R_4$ may represent any one selected from the group consisting of H, $CH_3$, $CH_2CH_3$, $CH_2CH_2CH_3$, $CH_2F$ and $CH_2Cl$.

Specifically, the first step comprises first reacting a compound of Chemical Formula 1 having both an alcohol functional group and a leaving group with a sulfonyl chloride derivative of Chemical Formula 2 to prepare an intermediate compound of Chemical Formula 3.

Specifically, the Reaction Scheme of the first step is as follows.

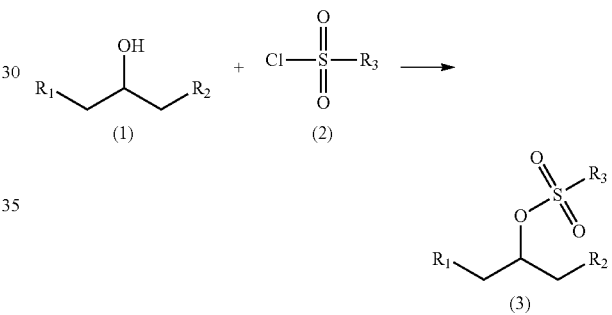

wherein, the $R_1$, $R_2$ and $R_3$ are as defined above.

At this time, the first step may be carried out in the presence of a base.

The base may be at least one selected from the group consisting of trimethylamine, pyridine, 1-methylimidazole, pyrrolidine, imidazole and morpholine, and preferably, triethylamine may be used, but is not limited thereto.

The equivalent ratio between the compound of Chemical Formula 1 and the compound of Chemical Formula 2 may be in the range of 0.5 to 1.5 equivalents, preferably 1.0 to 1.5 equivalents of the compound of Chemical Formula 2 to 1 equivalent of the compound of Chemical Formula 1. When the equivalent ratio is out of the above range, for example, when the compound of Chemical Formula 2 is used in an excessively small amount, the yield of the product may be lowered. When the compound of Chemical Formula 2 is used in an excessively large amount, there is a problem that the formed sultone ring is opened.

Further, the base may be used in an amount of 1.0 to 2.5 equivalents, preferably 1.0 to 1.5 equivalents. When the amount is out of the above range, the yield of the product may be lowered.

Further, the reaction of the first step is preferably carried out in a temperature range of −10 to 30° C., more preferably in a temperature range of 0° C. to 30° C. for 1 hour to 10 hours, more preferably for 1 hour to 5 hours.

Further, the reaction of the first step may be carried out in the presence of at least one solvent selected from the group consisting of dichloromethane, tetrahydrofuran, toluene, ethyl acetate and n-hexane. Preferably, dichloromethane or tetrahydrofuran may be used, and more preferably, tetrahydrofuran may be used, but is not limited thereto.

Specifically, the above-mentioned reaction is carried out by the steps of: dissolving the compound of Chemical Formula 1 in a solvent, lowering the temperature to −10 to 0° C., adding dropwise the compound of Chemical Formula 2, then adding dropwise the base, raising the temperature to room temperature and stirring the resulting mixture for 3 to 5 hours. Further, after completion of the reaction, it may comprise the steps of performing layer separation by adding ethyl acetate or the like, then washing the organic layer with hydrochloric acid, sodium hydrogencarbonate and/or saline, etc., drying and filtering, and then removing the solvent under reduced pressure to produce an intermediate compound of Chemical Formula 3.

The yield of the intermediate compound of Chemical Formula 3 may be 90 to 100%, preferably 95 to 98%.

Next, the reaction of the second step comprises cyclizing the sulfonate intermediate represented by Chemical Formula 3 to produce a sultone derivative represented by Chemical Formula 4.

Specifically, the Reaction Scheme of the second step is as follows.

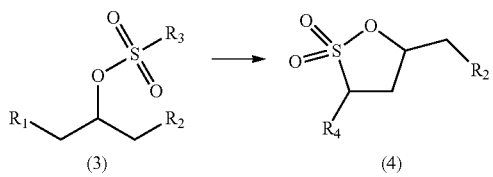

wherein, the $R_1$, $R_2$, $R_3$ and $R_4$ are as defined above.

The second step may be carried out in the presence of a base.

The base may be at least one selected from the group consisting of methyllithium, n-butyllithium, sec-butyllithium, tert-butyllithium, lithium diisopropylamide, lithium bis(trimethylsilane), lithium bis(trimethylsilyl)amide, lithium tetramethylpiperidine, potassium bis(trimethylsilyl) amide and sodium hydride, and preferably, lithium diisopropylamide may be used, but is not limited thereto.

The equivalent ratio between the compound of Chemical Formula 3 and the base may be in the range of 1.0 to 1.5 equivalents of the base to 1 equivalent of the compound of Chemical Formula 3. When the equivalent ratio is out of the above range, for example, when the compound of Chemical Formula 3 is used in an excessively small amount, the desired reaction may not take place. When the compound of Chemical Formula 3 is used in excess, there is a problem that the formed sultone ring is opened.

Further, the reaction of the second step may be carried out preferably in a temperature range of −90 to 30° C., more preferably in a temperature range of −80° C. to 25° C. for 1 hour to 6 hours, more preferably 1 hour to 5 hours.

Further, the reaction of the second step may be carried out in the presence of at least one solvent selected from the group consisting of dichloromethane, tetrahydrofuran, toluene, ethyl acetate and n-hexane, and preferably, dichloromethane or tetrahydrofuran may be used, and more preferably, tetrahydrofuran may be used, but is not limited thereto.

Specifically, the second step may be carried out through the steps of dissolving the intermediate represented by Chemical Formula 3 in a solvent, lowering the temperature −90 to −70° C., preferably −80 to −70° C., adding dropwise the base, then gradually raising the temperature to room temperature and stirring the resulting mixture for 2 to 4 hours, preferably about 3 hours. Further, after completion of the reaction, it may comprise producing a 1,3-propanesultone derivative of Chemical Formula 4 by lowering the temperature to about 0° C., adding ethyl acetateheate, etc., stirring the mixture for 20 minutes to 1 hour, preferably about 30 minutes, then removing the solvent under reduced pressure and purifying the result.

The yield of the sultone derivative represented by Chemical Formula 4 may be 30 to 95%, preferably 40 to 95%, particularly 70 to 95%.

Hereinafter, preferred examples will be presented to facilitate understanding of the present invention. However, these examples are provided for a better understanding of the present invention only, and are not intended to limit the scope of the invention.

EXAMPLE (Example 1-1) Preparation of 1-chloro-3-fluoro-2-methanesulfonate propanol 20 g of 1-chloro-3-fluoro-2-propanol was dissolved in 200 mL of tetrahydrofuran, the temperature was lowered to 0° C., 24.4 g of methanesulfonyl chloride was added dropwise, and then g of triethylamine was added dropwise thereto. Then, the temperature was raised to room temperature and the mixture was stirred for 4 hours. After completion of the reaction, 200 mL of ethyl acetate and 50 mL of $H_2O$ were added thereto. After layer separation, the organic layer was washed with 50 mL of 1N HCl, 50 mL of sat aq $NaHCO_3$ and 50 mL of brine, dried over $MgSO_4$, filtered and the solvent was removed under reduced pressure to obtain 1-chloro-3-fluoro-2-methanesulfonate propanol in a yield of 98%.

$^1$H NMR (400 MHz, $CDCl_3$) δ: 5.4 (m, 1H), 4.78 (m, 2H), 3.78 (d, 2H), 3.1 (s, 3H)

(Example 1-2) Preparation of 3-fluoromethyl 1,3-propanesultone 6.0 g of 1-chloro-3-fluoro-2-methanesulfonate propanol was dissolved in 60 mL of tetrahydrofuran, the temperature was lowered to −78° C., and 23 mL of LDA was slowly added dropwise thereto. Then, the temperature was gradually raised to room temperature, and the mixture was stirred for 3 hours. After completion of the reaction, the temperature was lowered to 0° C., 30 mL of ethyl acetate was added thereto, and the mixture was stirred for 30 minutes. The solvent was then removed under reduced pressure and purified to obtain 3-fluoromethyl 1,3-propanesultone in a yield of 70%.

$^1$H NMR (400 MHz, $CDCl_3$) δ: 4.8 (m, 1H), 4.60 (m, 2H), 3.34 (m, 2H), 2.71 (m, 2H)

(Example 2-1) Preparation of 1,3-dichloro-2-methanesulfonate propanol 50 g of 1,3-dichloro-2-propanol was dissolved in 500 ml of tetrahydrofuran, the temperature was lowered to 0° C., and 49 g of methanesulfonyl chloride was added dropwise thereto. Then, 51 g of triethylamine was slowly added dropwise, the temperature was gradually raised to room temperature, and the mixture was stirred for 4 hours. After completion of the reaction, the reaction mixture was washed with 500 mL of ethyl acetate and 75 mL of $H_2O$. After layer separation, the organic layer was washed with 75 mL of 1N HCl, 75 mL of sat aq $NaHCO_3$ and 75 mL of brine, dried over $MgSO_4$, filtered, and then the solvent was removed under reduced pressure to obtain 1,3-dichloro-2-methanesulfonate propanol in a yield of 95%.

$^1$H NMR (400 MHz, $CDCl_3$) δ: 4.95 (m, 1H), 3.84 (m, 4H), 3.15 (s, 3H)

(Example 2-2) Preparation of 3-chloromethyl 1,3-propanesultone 5.0 g of 1,3-dichloro-2-methanesulfonate propanol was dissolved in 50 ml of tetrahydrofuran, and the temperature was lowered to −78° C. Then, 17.7 mL of LDA was slowly added dropwise thereto, and then the temperature was raised to room temperature and the mixture was stirred for 3 hour. After completion of the reaction, the temperature was lowered to 0° C., and 30 mL of ethyl acetate was added thereto. The reaction mixture was stirred for 30 minutes, and then the solvent was removed under reduced pressure and purified to obtain 3-chloromethyl 1,3-propanesultone in a yield of 70%.

$^1$H NMR (400 MHz, $CDCl_3$) δ: 4.82 (m, 1H), 3.72 (m, 2H), 3.34 (m, 2H), 2.56 (m, 2H)

(Example 3-1) Preparation of 1-chloro-3-fluoro-2-ethanesulfonate propanol 10.0 g of 1-chloro-3-fluoro-2-propanol was dissolved in 100 mL of tetrahydrofuran, and the temperature was lowered to 0° C. and 12.6 g of ethanesulfonyl chloride was added dropwise, and then 11.7 g of triethylamine was slowly added dropwise thereto. The temperature was gradually raised to room temperature and the mixture was stirred for 4 hours. After completion of the reaction, 100 mL of ethylacetate and 20 mL of $H_2O$ were added. After layer separation, the organic layer was washed with 25 mL of 1N HCl, 25 mL of sat aq $NaHCO_3$ and 25 mL of brine, dried over $MgSO_4$, filtered, and then the solvent was removed under reduced pressure to obtain 1-chloro-3-fluoro-2-ethanesulfonate propanol in a yield of 98%.

$^1$H NMR (400 MHz, $CDCl_3$) δ: 4.99 (m, 1H), 4.76 (q, 2H), 3.79 (q, 2H), 3.25 (q, 2H), 1.47 (t, 3H)

(Example 3-2) Preparation of 3-fluoromethyl-1-methyl 1,3-propanesultone 5.0 g of 1-chloro-3-fluoro-2-ethanesulfonate propanol was dissolved in 50 mL of tetrahydrofuran, the temperature was lowered to −78° C., 35.8 mL of LDA was added dropwise thereto. Then, the temperature was gradually raised to room temperature and the mixture was stirred for 3 hours. After completion of the reaction, the temperature was lowered to 0° C., and 30 mL of ethyl acetate was added thereto, and the mixture was stirred for 30 minutes. Then, the solvent was removed under reduced pressure and purified to obtain 3-fluoromethyl-1-methyl 1,3-propanesultone in a yield of 88%.

$^1$H NMR (400 MHz, $CDCl_3$) δ: 4.69 (m, 3H), 3.48 (m, 1H), 2.63 (m, 1H), 2.36 (m, 1H), 1.51 (m, 3H)

(Example 4-1) Preparation of 1,3-dichloro-2-ethanesulfonyl-propanol 50.0 g of 1,3-dichloro-2-propanol was dissolved in 500 mL of tetrahydrofuran, the temperature was lowered to 0° C., and 54.8 g of ethanesulfonyl chloride was added dropwise, and then, 51 g of triethylamine was slowly added dropwise thereto. The temperature was raised to room temperature and the mixture was stirred for 4 hours. After completion of the reaction, the reaction mixture was washed with 500 mL of ethyl acetate and 75 mL of $H_2O$. After layer separation, the organic layer was washed with 75 mL of 1N HCl, 75 mL of sat aq $NaHCO_3$ and 75 mL of brine, dried over $MgSO_4$, filtered, and then the solvent was removed under reduced pressure to obtain 1,3-dichloro-2-ethanesulfonyl-propanol in a yield of 95%.

$^1$H NMR (400 MHz, $CDCl_3$) δ: 4.96 (m, 1H), 3.85 (t, 4H), 3.27 (q, 2H), 1.47 (t, 3H)

(Example 4-2) Preparation of 3-chloromethyl-1-methyl 1,3-propanesultone 5.0 g of 1,3-dichloro-2-ethanesulfonyl-propanol was dissolved in 50 mL of tetrahydrofuran, the temperature was lowered to −78° C., and 18 mL of LDA was added dropwise thereto. Then, the temperature was gradually raised to room temperature, and the mixture was stirred for 4 hours. After completion of the reaction, the temperature was lowered to 0° C., 30 mL of ethyl acetate was added, and the mixture was stirred for 30 minutes. Then, the solvent was removed under reduced pressure and purified to obtain 3-chloromethyl-1-methyl 1,3-propanesultone in a yield of 88%.

$^1$H NMR (400 MHz, $CDCl_3$) δ: 4.17 (m, 1H), 3.77 (m, 1H), 3.50 (m, 1H), 2.63 (m, 1H), 2.12 (m, 1H), 1.51 (m, 3H)

(Example 5-1) Preparation of 3-chloro-1-fluoro-2-propanesulfonate propanol 10 g of 3-chloro-1-fluoropropanol was dissolved in 100 ml of tetrahydrofuran, the temperature was lowered to 0° C., and 13.9 g of propanesulfonyl chloride was slowly added dropwise thereto. Then, 10.8 g of triethylamine was slowly added dropwise, the temperature was gradually raised to room temperature and the mixture was stirred for 4 hours. After completion of the reaction, the temperature was lowered to 0° C., and the reaction mixture was washed with 100 mL of ethyl acetate and 25 mL of $H_2O$. After layer separation, the organic layer was washed with 25 mL of 1N HCl, 25 mL of sat aq $NaHCO_3$ and 25 mL of brine, dried over $MgSO_4$, filtered, and then the solvent was removed under reduced pressure to obtain 3-chloro-1-fluoro-2-propanesulfonate propanol in a yield of 98%.

$^1$H NMR (400 MHz, $CDCl_3$) δ: 5.0 (m, 1H), 4.70 (dd, 2H), 3.70 (r, 2H), 3.30 (t, 2H), 2.0 (m, 2H), 1.1 (t, 3H)

(Example 5-2) Preparation of 1-ethyl-3-fluoromethyl 1,3-propanesultone 5.0 g of 3-chloro-1-fluoro-2-propanesulfonate propanol was dissolved in 50 ml of tetrahydrofuran, the temperature was lowered to −78° C., and 15 mL of LDA was added dropwise thereto. Then, the temperature was gradually raised to room temperature and the mixture was stirred for 4 hours. After completion of the reaction, the temperature was lowered to 0° C., and 30 mL of ethyl acetate was added, and the mixture was stirred for 30 minutes. Then, the solvent was removed under reduced pressure and purified to obtain 1-ethyl-3-fluoromethyl 1,3-propanesultone in a yield of 40%.

$^1$H NMR (400 MHz, $CDCl_3$) δ: 4.78 (m, 1H), 3.77 (m, 2H), 3.50 (m, 1H), 2.63 (m, 1H), 2.12 (m, 1H), 1.51 (m, 3H)

(Example 6-1) Preparation of 1,3-dichloro-2-propanesulfonate propanol 10 g of 1,3-dichloro-2-propanol was dissolved in 100 ml of tetrahydrofuran, the temperature was lowered to 0° C., and 12.2 g of propylsulfonyl chloride was slowly added dropwise thereto. Then, 9.41 g of triethylamine was added dropwise, the temperature was gradually raised to room temperature, and the mixture was stirred for 4 hours. After the completion of the reaction, the temperature was lowered to 0° C., and the reaction mixture was washed with 100 mL of ethylacetate and 25 mL of $H_2O$. After layer separation, the organic layer was washed with 25 mL of 1N HCl, 25 mL of sat aq $NaHCO_3$ and 25 mL of brine, dried over $MgSO_4$, filtered, and then the solvent was removed under reduced pressure to obtain 1,3-dichloro-2-propanesulfonate propanol in a yield of 98%.

$^1$H NMR (400 MHz, $CDCl_3$) δ: 4.96 (m, 1H), 3.84 (t, 4H), 3.21 (t 2H), 1.96 (m, 2H), 1.10 (t, 3H)

(Example 6-2) Preparation of 3-chloromethyl-1-ethyl 1,3-propane sultone 5 g of dichloro-2-propanesulfonate propanol was dissolved in 50 ml of tetrahydrofuran and the temperature was lowered to −78° C. 17 mL of LDA was added dropwise thereto, the temperature was gradually raised to room temperature, and the mixture was stirred for 4 hours. After completion of the reaction, the temperature was lowered to 0° C., 30 mL of ethyl acetate was added and the mixture was stirred for 30 minutes. Then, the solvent was removed under reduced pressure and purified to obtain 3-chloromethyl-1-ethyl-1,3-propanesultone in a yield of 77%.

$^1$H NMR (400 MHz, $CDCl_3$) δ: 4.78 (m 1H), 3.77 (m, 2H), 3.50 (m, 1H), 2.63 (m, 1H), 2.12 (m, 1H), 1.51 (m, 3H)

The invention claimed is:

1. A method for preparing a sultone derivative represented by the following Chemical Formula 4, the method comprising the steps of:
   1) reacting an alcohol represented by the following Chemical Formula 1 with a sulfonyl chloride derivative represented by the following Chemical Formula 2 to prepare an intermediate represented by the following Chemical Formula 3; and
   2) cyclizing the intermediate represented by the Chemical Formula 3 to prepare the sultone derivative represented by the Chemical Formula 4;

[Chemical Formula 1]

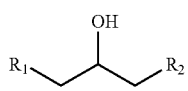

[Chemical Formula 2]

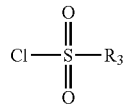

[Chemical Formula 3]

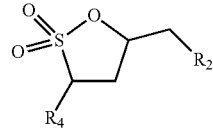

[Chemical Formula 4]

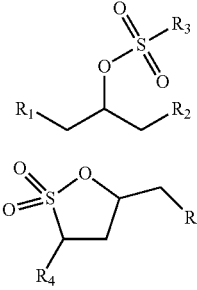

wherein, $R_1$, $R_2$, $R_3$ and $R_4$ represent each independently hydrogen, a halogen atom, an unsubstituted C1-C10 alkyl group or a C1-C10 alkyl group substituted with halogen; wherein the first step and the second step are carried out in the presence of at least one solvent.

2. The method for preparing a sultone derivative according to claim 1, wherein the first step and the second step are carried out in the presence of a base.

3. The method for preparing a sultone derivative according to claim 2, wherein the base used in the first step is at least one selected from the group consisting of triethylamine, pyridine, 1-methylimidazole, pyrrolidine, imidazole and morpholine.

4. The method for preparing a sultone derivative according to claim 2, wherein the base used in the second step is at least one selected from the group consisting of methyl lithium, butyl lithium, sec-butyllithium, tert-butyllithium, lithium diisopropylamide, lithium bistrimethylsilane, lithium tetramethylpiperidine, potassium bistrimethylsilylamide and sodium hydride.

5. The method for preparing a sultone derivative according to claim 1, wherein the first step and the second step are carried out in the presence of at least one solvent selected from the group consisting of dichloromethane, tetrahydrofuran, toluene, ethyl acetate and n-hexane.

6. The method for preparing a sultone derivative according to claim 1, wherein the first step is carried out at a temperature of −10 to 30° C.

7. The method for preparing a sultone derivative according to claim 1, wherein the second step is carried out at a temperature of −90 to 10° C.

8. The method for preparing a sultone derivative according to claim 1, wherein the $R_1$ and $R_2$ are each independently a halogen atom, and the $R_3$ and $R_4$ are each independently hydrogen, an unsubstituted C1-C4 alkyl group, or a C1-C4 alkyl group substituted with halogen.

* * * * *